United States Patent [19]

Gelfand

[11] 4,005,153
[45] Jan. 25, 1977

[54] POLYHALOCYCLOPENTENYL PHENYL COMPOUNDS

[75] Inventor: Samuel Gelfand, Niagara Falls, N.Y.

[73] Assignee: Hooker Chemicals & Plastics Corporation, Niagara Falls, N.Y.

[22] Filed: June 9, 1975

[21] Appl. No.: 585,207

Related U.S. Application Data

[60] Continuation of Ser. No. 381,846, July 23, 1973, which is a division of Ser. No. 142,054, May 10, 1971, Pat. No. 3,839,454, which is a continuation-in-part of Ser. No. 758,684, Sept. 10, 1968, which is a continuation-in-part of Ser. No. 318,522, Oct. 24, 1963, Pat. No. 3,450,768.

[52] U.S. Cl. .......................... 260/650 R; 424/353
[51] Int. Cl.² .................................. C07C 25/18
[58] Field of Search ................ 260/650 R, 650 F

[56] References Cited

UNITED STATES PATENTS 3,283,017  11/1966  Weil ........................... 260/650 R

OTHER PUBLICATIONS

Markl et al., Chemische Ber. 1962, pp. 2852–2860.

*Primary Examiner*—D. Horwitz
*Attorney, Agent, or Firm*—Peter F. Casella; William J. Crossetta, Jr.

[57] ABSTRACT

There are provided compounds of the formulae

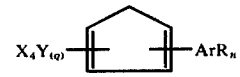

wherein:

X is a halogen atom, such as chlorine and bromine;

Y is selected from the group consisting of halogen, such as chlorine and bromine, an alkyl radical and hydrogen, at least one of said Y substituents being halogen;

R is selected from the group consisting of chlorine, bromine, fluorine and trifluoromethyl;

Ar is an aromatic nucleus containing a hydrogen substituent on a ring position adjacent to the point of polyhalocyclopentadiene or polyhalocyclopentenone attachments, aromatic being defined herein as a derivative of benzene or a carbon compound which contains one or more carbon rings; and n is from 2 to 4, z is from 1 to 2 inclusive, q is a number from 0 to 1, said q being 0 when z is 2.

The compounds of this invention are pesticidal, being especially effective as nematocides.

7 Claims, No Drawings

POLYHALOCYCLOPENTENYL PHENYL COMPOUNDS

This is a continuation of Ser. No. 381,846, filed July 23, 1973, which is a division of Ser. No. 142,054, filed May 10, 1971, now U.S. Pat. No. 3,839,454, which is a continuation-in-part of abandoned application Ser. No. 758,684, filed Sept. 10, 1968 which is a continuation-in-part of application Ser. No. 318,522 filed Oct. 24, 1963, now U.S. Pat. No. 3,450,768.

This invention relates to new compositions of matter. More specifically, the present invention is concerned with polyhalocyclopentenyl compounds which are the products produced by the reaction of polyhalocyclopentadienes and polyhalocyclopentenones with an aromatic compound.

In accordance with the present invention a compound selected from the group consisting of polyhalocyclopentadienes and polyhalocyclopentenones are reacted with a substituted aromatic compound having at least two adjacent unsubstituted ring positions available for reaction in the presence of a Friedel-Crafts catalyst.

The reaction occurring can be illustrated by the following specific equations which are not intended to be limiting:

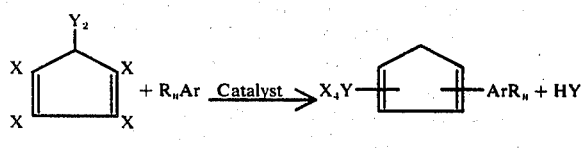

(I)

Polyhalocyclopentadiene

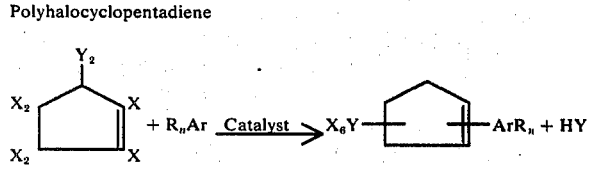

(II)

Polyhalocyclopentene

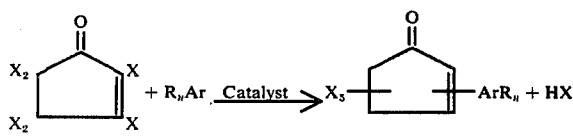

(III)

Polyhalocyclopentenone

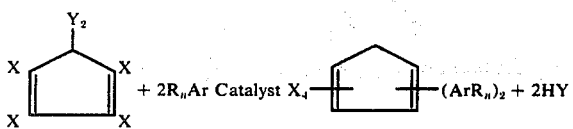

(IV)

wherein

X is a halogen atom, such as chlorine and bromine;

Y is selected from the group consisting of halogen, such as chlorine and bromine, an alkyl radical and hydrogen, at least one of said Y substituents being halogen;

R is selected from the group consisting of chlorine, bromine, fluorine and trifluoromethyl;

$n$ is from 2 to 4 and

Ar is an aromatic nucleus containing unsubstitution, by R groups, in at least two adjacent ring positions for reaction, aromatic being defined herein as a derivative of benzene or a carbon compound which contains one or more carbon rings.

The novel compounds of the present invention are represented by the following formulas:

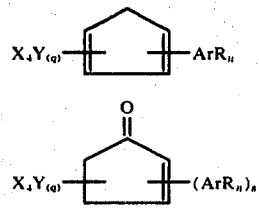

wherein $s$ is from 1 to 2 inclusive, $q$ is a number from 0 to 1, said $q$ being zero when $s$ is two, and the remaining substituents are as described herein.

Illustrative examples of the polyhalocyclopentadienes which can be utilized as a reactant in the process of the present invention include hexachlorocyclopentadiene, hexabromocyclopentadiene, pentachlorocyclopentadiene, bromopentachlorocyclopentadiene, alkylpentachlorocyclopentadiene, e.g. methyl, ethyl, hexyl, isopropyl, decyl pentachlorocyclopentadiene, dibromotetrachlorocyclopentadiene, and the like. Also, mixed halogenated polyhalocyclopentadienes, such as dichlorotetrabromocyclopentadiene may be used.

Among the polyhalocyclopentenones which are suitable as reactants in the process of the present invention are hexachlorocyclopentanone, hexabromocyclopentanone, dibromotetrachlorocyclopentanone, bromopentachlorocyclopentanone, alkylpentachlorocyclopentanone such as the methyl, ethyl, hexyl, heptyl, and octylpentachlorocyclopentanone, alkylbromotetrachlorocyclopentanone, such as, e.g., the methyl, ethyl, hexyl, and octylbromotetrachlorocyclopentanone, and the like. Other polyhalocyclopentanones, such as trichlorotribromocyclopentanone, alkyldichlorotetrabromocyclopentanone, etc. can also be employed.

The alkyl radicals, which generally contain from 1 to about 20 carbons, and preferably from 1 to 8 carbon atoms include, for example, methyl, ethyl, isopropyl, butyl, pentyl, hexyl, heptyl, oxtyl, dodecyl, and the like, as Y substituents on the reactants.

Illustrative of the substituted aromatic compounds which may be utilized as haloaromatic reactants in the process of the present invention which generally contain from 6 to 14 carbon atoms are orthodichlorobenzene, metadichlorobenzene, paradichlorobenzene, paradibromobenzene, 1,2,3-tri-chlorobenzene, 1,2,4-trichlorobenzene, 1,2,3,4-tetrachlorobenzene, metachlorobenzotrifluoride, meta and para xylene hexafluoride, and the like. Other substituted aromatic hydrocarbons of the type described herein which will not adversely affect the reaction mechanism can be employed.

Illustrative examples of the Friedel-Crafts catalysts are aluminum chloride, aluminum bromide, ferric chloride, and the like. Only a catalytic amount is normally required generally in the range of 0.01 percent to 10 percent by weight, with the preferred range being 0.1 to 2 percent.

Monoaryl or diaryl polyhalocyclopentadienes and polyhalocyclopentenones are formed, the major product being formed depending on the ratio of reagents employed. For example, when up to one mole of substituted aromatic compound is employed, the major product resulting is the monoaryl polyhalocyclopentadiene or polyhalocyclopentenone, while with greater than 1 mole an increase in the amount of the diaryl product results. Thus when two moles of substituted aromatic compound are utilized the product is substantially a diarylpolyhalocyclopentadiene or a diarylcyclopentenone.

The reaction is generally accomplished by heating the reactants in the presence of a Friedel-Crafts catalyst until the reaction is complete, as evidenced by the evolution of the required amount of hydrogen halide.

The reaction temperature will vary with the type of catalyst being employed, but generally is in the range of 50° to 275° centigrade, with a preferred range being from 60° to about 135° centigrade. For aluminum chloride the temperature will generally be in the range of about 50° centigrade to about 150° centigrade. With ferric chloride as the catalyst, higher temperatures are employed, generally in the range of about 125° centigrade to 250° centigrade.

A solvent is not generally necessary, but one can be used to moderate or facilitate the reaction. Among the solvents which can be used are perchloroethylene, carbon tetrachloride, and the like. Other solvents of high enough boiling point to maintain the required reaction temperature which do not react with either of the selected starting reagents or the catalyst to adversely affect the reaction mechanism can also be employed.

However, the use of a solvent such as perchloroethylene or carbon tetrachloride will usually require a higher operating temperature. Thus for any particular reaction, the temperature selected will generally depend on the catalyst, the solvent, and the reactivity of reagents.

The reaction product is isolated by methods known in this art. For example, in the case of liquid products, the catalyst is removed by washing with aqueous hydrochloric acid and the product is isolated by distillation. The diaryl products, which are usually solids, are conveniently isolated by triturating the reaction mixture with acetone to remove the catalyst and filtering of the solid product.

The ratio of the starting materials may be varied but will usually depend on the product desired. Generally equimolar amounts of reagents are used to prepare monoaryl derivatives and a ratio of 2 moles of aromatic compound to one mole of polyhalocyclopentadiene, polyhalocyclopentene, or polyhalocyclopentenone when diaryl derivatives are desired.

Typical equations illustrating the process and the compositions of the present invention follow:

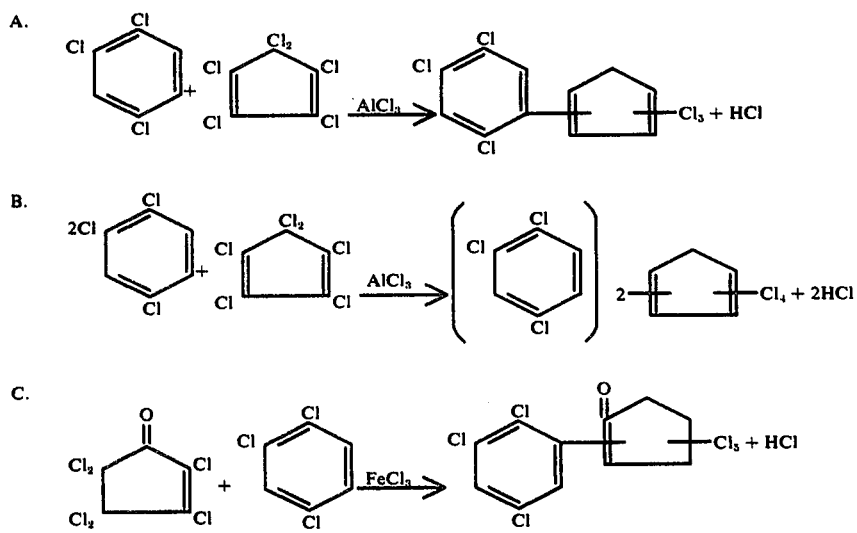

D. 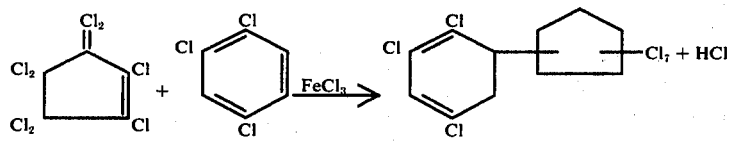

Both the monoaryl and diaryl compounds have utility as fire retardant additives in paints, plastics, fabric treatment, etc. In addition, the monoaryl compounds themselves and certain compounds prepared from them have utility as herbicides, fungicides and insecticides. For example, the bicycloheptadiene Diels-Alder adduct of 1,2,4-trichlorophenylpentachlorocyclopentadiene, as represented by the structure

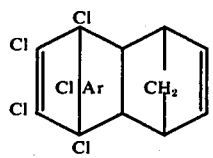

shows activity as a miticide.

Also trichlorophenyltetrachloropentadienoic acid prepared by the following sequence of reactions has activity as a herbicide.

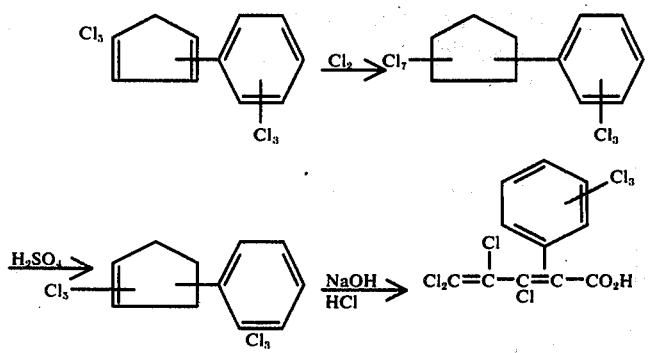

In order that those skilled in the art may better understand the present invention and the manner in which it may be practiced, the following illustrative examples are given.

In the specification, examples, and claims, parts are by weight and temperatures are in degrees centigrade, unless otherwise stated.

EXAMPLE 1

Preparation of 2,4-dichlorophenyl pentachlorocyclopentadiene

A mixture of 294 grams (2.0 moles) of paradichlorobenzene, 819 grams (3.0 moles) of hexachlorocyclopentadiene, and 15 grams of aluminum chloride, in 300 grams of perchloroethylene was heated at 80°–92° centigrade for two hours during which time a total of 103 grams of hydrogen chloride was evolved. Ten milliliters of water and 20 grams of Superfiltrol absorbent were added and the reaction mixture was stirred at 60° centigrade for 30 minutes and then filtered with suction. The filtrate was distilled at reduced pressure and the fraction boiling at 131°–160° centigrade at 0.5 to 2.3 millimeters of mercury pressure was collected and refractionated through a one foot long heated Vigreux column to give pure 2,4-dichlorophenyl pentachlorocyclopentadiene as a pale yellow viscous oil of boiling point of 146°–147° centigrade at 0.4–0.6 millimeters of mercury.

Analysis: Calculated for $C_{11}H_3Cl_7$ - percent chlorine 64.7 Found 64.8 Molecular weight (determined by vapor pressure osmometer in ethanol and in benzene) 377.4; Theoretical 383.5.

In a similar manner, the corresponding bromine compound, 2,4-dibromophenyl pentabromocyclopentadiene, is prepared by employing paradibromobenzene and hexabromocyclopentadiene in the place of paradichlorobenzene and hexachlorocyclopentadiene.

Example 2

Preparation of

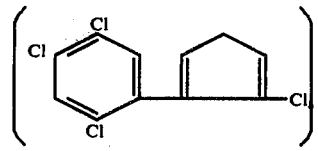

1,2,4-Trichlorophenyl pentachlorocyclopentadiene

| | |
|---|---|
| Hexachlorocyclopentadiene | 819.6 grams (3.0 moles) |
| 1,2,4-Trichlorobenzene | 363 grams (2.0 moles) |
| AlCl₃ | 14 grams (0.1 mole) |
| Perchloroethylene | 300 grams | were charged into a two liter, 3-necked flask equipped with a stirrer, thermometer, water condenser and a water trap to absorb hydrogen chloride. The mixture was stirred and heated at 90°–95° centigrade for 5 hours until a total of 73 grams of HCl was collected. The reaction mixture was diluted with 300 milliliters of perchloroethylene. The AlCl₃ was decomposed with 5 milliliters of water. 20 grams of filter aid and 5 grams of anhydrous sodium carbonate were added and the mixture was heated to 90° centigrade with stirring and was filtered with suction.

Perchloroethylene was distilled off at 20 millimeters of mercury pressure by means of water pump vacuum. The residue was fractionated at high vacuum. Unreacted starting materials were collected first, followed by the product, a pale yellow viscous oil boiling at 172°–176° centigrade at 0.55–0.63 millimeters of mercury pressure.

Analysis:

Calculated for total chlorine — Theoretical for $C_{11}H_2Cl_8$ 67.9%
Found: 67.5%

EXAMPLE 3

The corresponding bromine compound 1,2,4-tribromophenylpentabromo

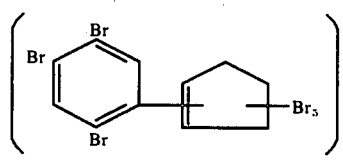

is similarly prepared by the method of Example 2, reacting hexabromocyclopentadiene and 1,2,4-tribromobenzene instead of hexachlorocyclopentadiene and 1,2,4-trichlorobenzene of Example 2.

EXAMPLE 4

This example shows the use of ferric chloride as a catalyst for the reaction of hexachlorocyclopentadiene and 1,2,4-trichlorobenzene.

A mixture of hexachlorocyclopentadiene, 546 grams (2.0 moles), 1,2,4-trichlorobenzene, 181.5 grams (1.0 mole), and 10 grams of $FeCl_3$ was stirred and heated at 180°–190° centigrade for 14 hours during which time 33 grams of HCl was evolved. The reaction mixture was diluted with 200 milliliters of benzene and 500 milliliters of perchloroethylene, washed with 100 milliliters of aqueous HCl, aqueous $NaHCO_3$ and finally, distilled water, dried and distilled. After distillation of the solvents and unreacted starting materials, the 1,2,4-trichlorophenylpentachlorocyclopentadiene product

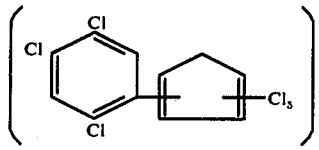

was collected as a pale yellow viscous oil boiling point 160°/0.3–0.45 millimeters weight 70 grams. The diarylation product di(1,2,4-trichlorophenyl)tetrachlorocyclopentadiene remained as a distillation residue, weight 256 grams.

In a similar manner, 1,2,4-trichlorophenyl methyltetrachlorocyclopentadiene is prepared by employing methyl pentachlorocyclopentadiene in place of the hexachlorocyclopentadiene.

EXAMPLE 5

In the manner of Example 4, 1,2,4-trichlorophenylmethylhexachlorocyclopentene

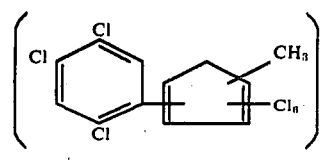

is prepared by using methylheptachlorocyclopentene in place of hexachlorocyclopentadiene.

Likewise, 1,4-dichlorophenylmethylhexachlorocyclopentene is prepared by using 1,4-dichlorobenzene in place of 1,2,4-trichlorobenzene.

EXAMPLE 6

Preparation of di(tetrachlorophenyl)tetrachlorocyclopentadiene

A mixture of 1,2,3,4-tetrachlorobenzene, 130 grams (0.6 mole), hexachlorocyclopentadiene, 65 grams (0.24 mole), and aluminum chloride, 5 grams, was heated on a steam bath at 75°–90° centigrade until the evolution of hydrogen chloride stopped and the reaction mixture solidified. The purple solid was triturated with acetone to dissolve the aluminum chloride, filtered, washed with acetone and dried to give a tan, solid product.

Analysis:

Calculated for $C_{17}H_2Cl_{12}$ — Percent Chlorine:
Theory: 67.4
Found: 67.8

EXAMPLE 7

Diels-Alder Adduct of Bicyclopentadiene and

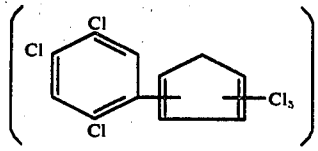

1,2,4-Trichlorophenyl pentachlorocyclopentadiene

A mixture of bicycloheptadiene, 46 grams (0.5 mole) and (1,2,4-trichlorophenyl)pentachlorocyclopentadiene, 21 grams (0.05 mole) was heated on a steam bath at 93°–5° centigrade for 24 hours. Excess bicycloheptadiene was removed by distillation to give the Diels-Alder reaction product, which crystallized on standing. The product was tested as a miticide, by spraying an aqueous dispersion of it on mites at a concentration of 1000 parts per million and resulted in 100 percent control after 5 days.

EXAMPLE 8

1,2,4-trichlorophenylheptachlorocyclopentene by Chlorination of 1,2,4-trichlorophenylpentachlorocyclopentadiene

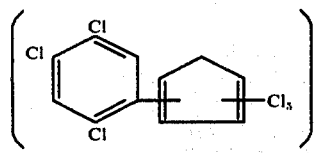

42 grams (0.1 mole) of 1,2,4-trichlorophenylpentachlorocyclopentadiene was dissolved in 243 milliliters of carbon tetrachloride and was chlorinated with catalysis by ultraviolet light at reflux until the absorption of chlorine ceased. Excess dissolved chlorine and the carbon tetrachloride were distilled off at atmospheric pressure on the steam bath and the product was collected by distillation at high vacuum, boiling point was 199°–201° centigrade at 0.5 millimeter of mercury pressure.

Analysis:

Calculated for $C_{11}H_2Cl_{10}$ — Percent Chlorine:
Theoretical: 72.6
Found: 73.2

EXAMPLE 9

Condensation of 1,2,4-Trichlorobenzene and Octachlorocyclopentene

A mixture of 1,2,4-trichlorobenzene, 454 grams (2.5 moles), octachlorocyclopentene, 1032 grams (3.0 moles), and ferric chloride, 15 grams, was heated at 165°–182° centigrade for 10 hours during which time 91 grams (2.5 moles) of HCl were evolved. The product was dissolved in 600 milliliters benzene, washed with 200 milliliters concentrated HCl to remove catalyst and then with water until neutral, dried, and distilled. The fraction boiling at 191°–205° centigrade at 0.2–0.3 millimeter was collected and analyzed for chlorine.

Analysis:

Calculated for $C_{11}H_2Cl_{10}$ — Percent Chlorine:
Theoretical: 72.6
Found: 71.8

EXAMPLE 10

1,2,4-Trichlorophenyl pentachlorocyclopentenone

Analysis: Calculated for $C_{11}H_2Cl_{10}$ - Percent Chlorine:
Theoretical:    72.6
Found:          71.8

Example 10
1,2,4-Trichlorophenyl pentachlorocyclopentenone

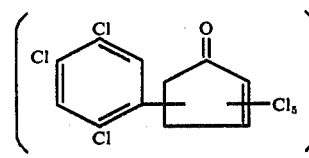

A mixture of 337 grams of 1,2,4-trichlorophenylheptachlorocyclopentene and 301 grams of concentrated sulfuric acid was stirred and heated at 105° to 124° centigrade for 10 hours. A total of 47 grams of hydrogen chloride was evolved and collected. The reaction mixture was mixed with water, the organic layer was separated and washed with water until neutral, after which it was dried and distilled. The product was collected as a red-orange viscous oil which crystallized on standing. Boiling point was 174°–178° centigrade at 0.4 millimeter of mercury pressure. Yield was 262 grams.

EXAMPLE 11

Hexachlorocyclopentenone, 96 grams (0.33 mole), 1,2,4-trichlorobenzene, 66 grams (0.33 mole) and ferric chloride, 5 grams, were heated and stirred together at 170° centigrade for 5 hours, during which time 6.5 grams (0.18 mole) of hydrogen chloride were evolved. The reaction mixture was dissolved in 100 milliliters of perchloroethylene, washed with 100 milliliters of 20 percent hydrochloric acid, then with water, dried and distilled. After solvent and unreacted starting materials were distilled off, the product was collected. Boiling point was 171°–186° at 0.2–0.3 millimeter. Yield was 57 grams.

EXAMPLE 12

1,2,4-Trichlorophenyl tetrachloropentadienoic acid 0.05 mole (22 grams) of 1,2,4-trichlorophenylpentachlorocyclopentenone was dissolved in benzene and stirred at 50° centigrade with 0.1 mole of aqueous sodium hydroxide until all of the base was consumed. The reaction mixture was acidified and the solid which separated was collected and recrystallized from aqueous ethanol. Melting point was 193°–196.5° centigrade, uncorrected. Neutralization Equivalent:

Calculated for $C_{11}H_3Cl_7O_2$
Theoretical: 415.5
Found: 416.6 and 410.4

In a similar manner to that of Example 12, the corresponding bromine compound 1,2,4-tribromophenylpentabromocyclopentenone is prepared by using pentabromocyclopentenone in place of hexachlorocyclopentenone.

The above examples are of preferred processes, in which Br and Cl were shown as examples of halogens for X and Y. Iodine and fluorine may also be employed in operative processes but are not usually considered to be preferred.

EXAMPLE 13

Bean plants infected with mites (Tetranychus telarius) were sprayed with a 0.025 percent aqueous dispersions of the bicycloheptadiene Diels-Alder adduct of 1,2,4-trichlorophenylpentachlorocyclopentadiene

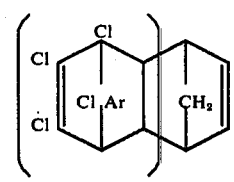

After 24 hours, 62 percent mortality of the mites was observed.

In a similar manner the 1,2,4-tribromophenylpentabromocyclopentadiene Diels-Alder adduct were sprayed on bean plants infected with mites with similar activity resulting.

For use as fire retardant additives in plastics, for example, the compounds of the present invention can be mixed by any one of several methods. The additives can be introduced into the polymer while the polymer is dissolved in a suitable solvent. This procedure is especially useful when it is desired to mix the additives during the polymer manufacturing process. When the polymer is subsequently recovered from the solvent, the additives are intimately mixed with the polymer. Usually the additives are mixed with the polymer in the molten state at temperatures that can range from the melting point to the decomposition temperature of the polymer. Alternatively the additives and polymer are dry-blended in the finely divided state so that an intimate mixture is obtained upon subsequent molding or extrusion. The halogenated compound of the instant invention is desirably incorporated in polymeric materials in the range from about 10 to about 50 percent by weight of the polymer composition, preferably from about 20 to about 35 percent by weight.

While there have been described various embodiments of the invention, the illustrations, methods and elements described are not intended to be understood as limiting the scope of the invention, as it is realized that changes and substitutions of equivalents therewithin are possible. It is intended that each element recited in any of the following claims is to be understood as referring to all equivalent elements for accomplishing substantially the same results in substantially the same or equivalent manner, it being intended to cover the invention broadly in whatever form its principle may be utilized.

What is claimed is:

1. A compound of the following formula:

$$X_4Y_{(q)} - \text{[cyclopentadiene]} - ArR_n$$

wherein:
a. X is a halogen selected from the group consisting of chlorine and bromine;
b. Y is selected from the group consisting of chlorine, bromine, hydrogen and an alkyl radical of from 1 to 8 carbon atoms;
c. R is selected from the group consisting of chlorine, bromine, fluorine and trifluoromethyl;
d. Ar is a phenyl radical having $R_n$ substituents and containing a hydrogen substituent on a ring position adjacent to the point of polyhalocyclopentadiene attachment; and
e. $n$ is an integer from 2 to 4 and $q$ is either 0 or 1.

2. A compound of claim 1 wherein R is selected from the group consisting of chlorine, bromine and fluorine.

3. The compound of claim 1, wherein:
a. X and Y are chlorine, and
b. $ArR_n$ is trichlorobenzene.

4. The compound of claim 1, wherein:
a. X and Y are chlorine, and
b. $ArR_n$ is dichlorobenzene.

5. The compound of claim 3 of the structure $$\text{[2,4,6-trichlorophenyl-pentachlorocyclopentadiene structure]}$$

6. The compound of claim 4 being 2,4-dichlorophenyl pentachlorocyclopentadiene.

7. The compound of claim 3 of the structure $$\text{[2,4,6-tribromophenyl-pentabromocyclopentadiene structure]}$$

A compound of the following formula:

$$X_4Y_{(q)} - \text{[cyclopentadiene]} - ArR_n$$

wherein:
a. X is a halogen selected from the group consisting of chlorine and bromine;
b. Y is selected from the group consisting of chlorine, bromine, hydrogen and an alkyl radical of from 1 to 8 carbon atoms;
c. R is selected from the group consisting of chlorine, bromine, fluorine and trifluoromethyl;
d. Ar is a phenyl radical having $R_n$ substituents and containing a hydrogen substituent on a ring position adjacent to the point of polyhalocyclopentadiene attachment; and
e. $n$ is an integer from 2 to 4 and $q$ is either 0 or 1.

UNITED STATES PATENT OFFICE
CERTIFICATE OF CORRECTION

PATENT NO. : 4,005,153
DATED : January 25, 1977
INVENTOR(S) : Samuel Gelfand

It is certified that error appears in the above-identified patent and that said Letters Patent are hereby corrected as shown below:

Column 8, line 44, "Bicyclopentadiene" should read --Bicycloheptadiene--. Column 9, under Example 10, delete --- Analysis: Calculated etc. ---. Column 10, line 60, parenthesis should be outside of the benzing ring. Column 12, line 31 thru 52, delete.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks